United States Patent
Jenkins et al.

(10) Patent No.: US 9,103,039 B2
(45) Date of Patent: Aug. 11, 2015

(54) QUATERNARY AMMONIUM CORROSION INHIBITOR

(75) Inventors: Alyn Jenkins, Aberdeen (GB); Neil Grainger, Stockton-on-Tees (GB); Michael Blezard, Huddersfield (GB); Mathieu Pepin, Grenoble (FR)

(73) Assignees: M-I Drilling Fluids U.K. Limited, Aberdeen (GB); Stepan UK Limited, Cheshire (GB)

( * ) Notice: Subject to any disclaimer, the term of this patent is extended or adjusted under 35 U.S.C. 154(b) by 717 days.

(21) Appl. No.: 13/319,186

(22) PCT Filed: May 7, 2010

(86) PCT No.: PCT/GB2010/000947
§ 371 (c)(1), (2), (4) Date: Jan. 27, 2012

(87) PCT Pub. No.: WO2010/128313
PCT Pub. Date: Nov. 11, 2010

(65) Prior Publication Data
US 2012/0128530 A1 May 24, 2012

(30) Foreign Application Priority Data

May 7, 2009 (GB) .................................. 0907886.6

(51) Int. Cl.
C23F 11/00 (2006.01)
C23F 11/14 (2006.01)
(Continued)

(52) U.S. Cl.
CPC ............. *C23F 11/141* (2013.01); *C07C 217/08* (2013.01); *C07C 219/06* (2013.01); *C07C 219/08* (2013.01); *C09K 8/54* (2013.01); *C23F 11/143* (2013.01)

(58) Field of Classification Search
CPC ......... C09K 3/00; C23F 11/00; C07C 217/08; C07C 219/06
USPC ................. 422/7; 250/390, 392; 252/390, 392
See application file for complete search history.

(56) References Cited

U.S. PATENT DOCUMENTS

| | | | |
|---|---|---|---|
| 5,627,144 | A | 5/1997 | Urfer et al. |
| 6,261,346 | B1 | 7/2001 | Breuer et al. |
| 7,160,507 | B2 | 1/2007 | Dahlmann et al. |

FOREIGN PATENT DOCUMENTS

| | | |
|---|---|---|
| DE | 43 34 365 A1 | 4/1995 |
| EP | 0 878 605 A2 | 11/1998 |
| EP | 1 457 585 A1 | 9/2004 |
| WO | 95/33379 A2 | 12/1995 |

OTHER PUBLICATIONS

International Search Report issued in PCT/GB2010/000947, mailed on Nov. 23, 2010, 4 pages.

(Continued)

*Primary Examiner* — Kevin Joyner
(74) *Attorney, Agent, or Firm* — Osha • Liang LLP (57) ABSTRACT

The present invention relates to a corrosion inhibitor for use in the oil and gas exploration, recovery and processing industries. In particular, the invention relates to a quaternary ammonium compound suitable for use as such a corrosion inhibitor, to the manufacture of the quaternary ammonium compound, to compositions containing it, and to methods of using it. Quaternary ammonium compounds of the invention have the formula (I) in which R is $C_{1-6}$ alkyl, $C_{2-6}$ alkenyl, aryl, aralkyl; X, Y, and Z are each independently hydrogen, or R1CO—, provided that at least one of X, Y and Z is R1CO, where R1 is $C_{5-23}$ alkyl or alkenyl containing 0, 1, 2 or 3 double bonds; D is $C_{2-6}$ alkylene; E is $C_{2-4}$ alkylene; p, q and r are each, independently, integers from 0 to 20, with the proviso that p+q+r is from 3 to 20; and $A^-$ is an anion.

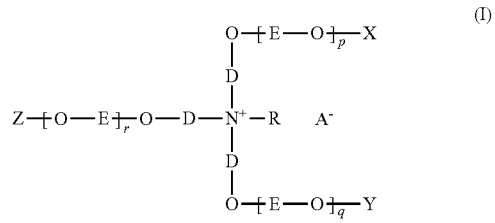

20 Claims, 2 Drawing Sheets

(51) Int. Cl.
*C07C 217/08* (2006.01)
*C07C 219/06* (2006.01)
*C07C 219/08* (2006.01)
*C09K 8/54* (2006.01)

(56) References Cited

OTHER PUBLICATIONS

Written Opinion issued in PCT/GB2010/000947, mailed on Nov. 23, 2010, 9 pages.

QUATERNARY AMMONIUM CORROSION INHIBITOR

The present invention relates to a corrosion inhibitor for use in the oil and gas exploration, recovery and processing industries. In particular, the invention relates to a quaternary ammonium compound suitable for use as such a corrosion inhibitor, to the manufacture of the quaternary ammonium compound, to compositions containing it, and to methods of using it.

Corrosion of metal surfaces is a major problem in the oil and gas exploration, recovery and processing industries. Corrosion inhibitors for use in these industries are designed to protect metal surfaces against the corrosive effects of water (fresh or brine), dissolved gases (H2S, O2, CO2), biological deposits, and weak and strong acids. Corrosion inhibitors are added to the liquids and gases which come into contact with metal surfaces and may protect against corrosion of those surfaces in a variety of ways. For instance, some corrosion inhibitors form a thin film or passivation layer on the metal surface, which acts as a barrier between the corrosive substance and the metal. Others reduce corrosion by taking part in physicochemical reactions at the metal surface.

Quaternary ammonium compounds have already been described for use as corrosion inhibitors for the production of petroleum and natural gas. For instance, U.S. Pat. No. 7,160,507 B (Clariant GmbH) discloses alkoxylated quaternary ammonium compounds for use in inhibiting corrosion of metallic devices employed in crude oil recovery, transportation and processing. The preferred compounds of this reference are doubly N-alkoxylated and carbonylated ammonium salts, which are reported to have excellent effectiveness as corrosion inhibitors, to exhibit improved film persistence, and good biodegradability. A particularly preferred group of compounds according to this reference is:

where $R^4$ is an organic radical containing 1 to 100 carbon atoms, $R^5$ is a $C_1$ to $C_{30}$ alkyl or $C_2$ to $C_{30}$ alkenyl group, n is a number of 1 to 20, preferably between 2 and 6, and $X^-$ is an anion. The reference exemplifies compounds in which $R^4$ is an alkyl group.

U.S. Pat. No. 6,261,346 B (Cognis Deutscland GmbH) discusses how certain quaternized ammonium compounds which contain at least one ester group in the molecule have a favourable corrosion-inhibiting effect, are readily biodegradable, and show low aquatic toxicity. Preferred quaternary ammonium compounds of this reference contain at least one group of formula:

where n is 2 or 3, p is between 1 and 3, and $R^5$ is an alkyl or alkenyl group containing 7 to 23 carbon atoms. Preferred compounds of the reference are obtained by the esterification of tertiary mono-, di- or trialkanolamines with fatty acid chlorides and subsequent quaternization of the esters. Generally the compounds contain one or two fatty acid ester groups. One such compound tested in this reference is methyl-N,N-bis-(coco-oxyethyl)-N-(2-hydroxyethyl)ammonium methosulphate.

The present invention provides alternative quaternary ammonium compounds for use as corrosion inhibitors. Preferred inhibitors of the invention are not only effective corrosion inhibitors, but also display good biodegradability. Furthermore, compared to known quaternary ammonium compounds, the inhibitors of the invention have a decreased tendency to promote formation of emulsions between oil and aqueous processing fluids. This is an important consideration in hydrocarbon extraction and recovery.

According to a first aspect, the present invention provides a quaternary ammonium compound of formula (I)

wherein:

R is an alkyl group containing 1 to 6 carbon atoms, an alkenyl group containing 2 to 6 carbon atoms, an aryl (e.g. preferably a $C_{5-20}$ aryl group, more preferably $C_{6-10}$ aryl group), or an aralkyl group (e.g. preferably $C_{1-6}$alkyl-$C_{5-20}$aryl, more preferably $C_{1-6}$alkyl-$C_{6-10}$aryl);

X, Y, and Z are each, independently hydrogen, or a group of formula R1CO—, provided that at least one of X, Y and Z is a group of formula R1CO, where R1 is an alkyl or alkenyl group containing 5 to 23 carbon atoms and 0, 1, 2 or 3 double bonds;

D is a $C_2$ to $C_6$ alkylene group;

E is a $C_2$ to $C_4$ alkylene group;

p, q and r are each, independently, integers from 0 to 20, with the proviso that p+q+r is from 3 to 20; and A– is an anion.

Preferably, R is a methyl group.

In preferred compounds, one of the groups X, Y and Z is R1CO and the other groups are hydrogen atoms. However, in some embodiments, the quaternary ammonium compound may be a diester compound, in which two of X, Y and Z are R1CO groups, or a triester, in which all three of X, Y and Z are R1CO groups.

The compound is preferably a monoester (in which one of the groups X, Y and Z is R1CO and the other groups are hydrogen atoms), but may be, or may include in admixture with it, diester and/or triester components. Where the monoester is in admixture with diester and/or triester components, the mixture preferably contains more monoester than diester or triester. In preferred mixtures, the amount of monoester present in the mixture is preferably more than about 40 mol. %, more preferably more than about 50 mol. %, even more preferably more than about 75 mol. % of the total quaternary ammonium ester content of the mixture.

Where the monoester compound is present in admixture with diester and triester components, the inventors have surprisingly found that when the admixture contains more monoester than diester or triester (or contains more than the specified minimum mol. % amounts of monoester listed above) the admixture exhibits improved properties as a component in corrosion inhibitor compositions (such as better oil quality when added to oil/brine emulsions, greater compatibility (e.g. solubility) in brine, and greater corrosion inhibition) when compared to compositions having monoester content outside these preferred ranges.

In preferred compounds, D is a $C_2$ to $C_4$ alkylene group, more preferably a —$CH_2CH_2$— group. Similarly, E is preferably a —$CH_2CH_2$— group. Preferably both groups are —$CH_2CH_2$— groups.

In preferred embodiments of quaternary ammonium compound of this aspect of the invention, each of p, q and r lies between 0 and 15, e.g. between 0 and 10, particularly preferably between 0 and 6. The total, p+q+r is preferably between 3 and 15, e.g. from 3 to 10, particularly preferably between 3 and 6.

One example of quaternary ammonium compound includes a cation having formula (II) below:

wherein each of p, q, r is independently 0, 1, 2 or 3, provided that p+q+r is 3. The compound is preferably a monoester, but may be, or may include in admixture with it, diester and/or triester components, preferably in the relative amounts defined above.

Another example of quaternary ammonium compound according to the first aspect of the invention includes a cation having formula (III) below:

wherein q+r lies between 3 and 15. In this case, preferred values of r+q include 4 and 6.

Although, the alkyl or alkenyl group, R1, may be straight or branched, straight chains are preferred. Where it is an alkenyl group, this preferably contains one double bond. Preferred R1 groups contain between 7 and 21 carbon atoms. Preferably the R1CO group is derived from a fatty acid, for instance from a fatty acid mixture, such as rapeseed oil fatty acids, soya oil fatty acids, tall oil fatty acids palm oil fatty acids or coconut oil fatty acids. However, other fatty acids are also suitable sources of R1CO group, eg caprylic acid, capric acid, lauric, myristic, palmitic, stearic, oleic, erucic, linoleic acid, linolenic acid, behenic acid, and mixtures of these.

In preferred embodiments of the first aspect of the invention, the group R1CO is the acyl group of rapeseed oil fatty acid. Thus, preferred compounds of the invention are those of formulae (I), (II), and (III) above, including at least one rapeseed fatty acyl group. Rapeseed fatty acid is a mixture of fatty acids mostly containing between 16 and 18 carbon atoms. Oleic acid is the predominant component, with smaller amounts of linoleic, linolenic, stearic and palmitic acids also present.

The anion A– included in the quaternary ammonium compound is not particularly limited. Generally the nature of this ion will depend on the method by which the quaternary ammonium compound is produced. Examples include halides, particularly chloride, methosulphate, and methophosphate. Of these, methosulphate is preferred.

In a second aspect, the invention provides a method of producing the quaternary ammonium compound of the first aspect comprising alkoxylation of a trialkanolamine followed by esterification and quaternisation. In a first step, a trialkanolamine such as triethanolamine, tripropanolamine, or tributanolamine, preferably triethanolamine is alkoxylated by reaction with an alkylene oxide such as ethylene oxide, propylene oxide, or butylene oxide, preferably ethylene oxide. The molar ratio of alkylene oxide to trialkanolamine used may be in the range 3-20:1, for instance 3-15:1, but is preferably about 3 or about 6. The alkoxylation can be carried out without a diluent, or in solution. Suitable solvents for the reaction are inert ethers such as dioxane or tetrahydrofuran. The reaction may be carried out uncatalysed, but is preferably catalysed, for instance by a basic compound such as an alkaline earth metal or alkali metal hydroxide or alkoxide. Alkali metal hydroxides, such as sodium hydroxide or potassium hydroxide are preferred.

The subsequent esterification step can be carried out with a fatty acid, R1COOH, or a suitable derivative thereof, such as an acid chloride or acid anhydride. Preferably, the alkoxylated trialkanolamine and the fatty acid are reacted in equimolar amounts, although the amount of fatty acid may be increased when it is desired to increase the level of esterification in the product. For example a 2:1 ratio of fatty acid to alkoxylated trialkanolamine may be used to obtain a product containing a higher proportion of di- and tri-ester products and relatively depleted in mono-ester.

As noted above, the inventors have surprisingly found that products that are relatively richer in monoester than di- or tri-ester generally exhibit improved properties (in terms of their usefulness in downhole applications). Therefore it is preferred that the method of producing the quaternary ammonium products includes reacting the alkoxylated trialkanolamine and the fatty acid in equimolar amounts so that this preferred product can be obtained.

After esterification the resulting tertiary amine compound is quaternised through the action of an alkylating agent. Examples of suitable alkylating agents include methyl chloride and dimethyl sulphate, of which the latter is preferred. Where R is an aralkyl group, the use of benzyl chloride is suitable.

The method of the second aspect is particularly suitable for production of compounds of formula (II) above.

In a third aspect, the invention provides a method of producing a compound of the first aspect comprising esterification of a trialkanolamine followed by alkoxylation and quaternisation. In this case, the trialkanolamine and fatty acid, or derivative thereof used for esterification are generally and preferably employed in equimolar amounts though, again, as discussed above more fatty acid can be used to increase the extent of esterification. Compounds and methods suitable for the esterification, are as described above. In the subsequent alkoxylation step, the esterified trialkanolamine may be reacted with between 3 and 20 equivalents of alkylene oxide, more preferably between 3 and 15, particularly preferably 4 or 6. The conditions for the alkoxylation reaction are as described above in respect of the second aspect. Quaternisation reagents suitable in the method of the second aspect of the invention are also suitable here.

The method of the third aspect results in a mixture of compounds including a compound of formula (III) above. However, transesterification during, and after the alkoxylation step results in a mixture of products within the general formula (I).

In a fourth aspect, the invention provides a corrosion inhibitor composition comprising the quaternary ammonium compound of the first aspect of the invention in aqueous solution. The composition may contain a mixture of quaternary ammonium compounds in accordance with the first aspect.

Preferably, the corrosion inhibitor composition of this aspect of the invention contains between about 5 and 50% by weight of the quaternary ammonium compound of the first aspect, preferably from about 10 to about 35%, more preferably from about 20 to about 30 weight percent.

The corrosion inhibitor composition of this aspect optionally includes other ingredients. For instance, the composition may include a water miscible organic solvent to assist in the dispersion and/or dissolution of the quaternary ammonium compound. This solvent component may be present at a level of up to 30 percent by weight of the composition, typically 5 to 30 weight percent. Preferably, it is present at a level not more than 20 percent by weight, most preferably at a level of 10 to 20 weight percent.

Examples of suitable water miscible solvents include C1-C6 alcohols such as isopropanol, ethylene glycol or propylene glycol, or mixtures thereof. However, preferred solvents are alkoxy alcohols, especially 2-butoxyethanol.

The compositions of the fourth aspect may also, optionally, contain a corrosion inhibitor intensifier, or synergist, at a level up to about 10 percent by weight of the composition, preferably at least about 0.1 percent. Particularly preferably, the intensifier is included at a level of between 2 and 6 percent, especially around 4% by weight. Preferred intensifiers for inclusion in the compositions of the fourth aspect include organic sulphur compounds. Examples of suitable organic sulphur compounds include mercapto alcohols, such as 2-mercaptoethanol, cysteamine hydrochloride, thioglycolic acid, thiourea, cystine, cysteine, 3,3'-dithiodipropionic acid and tert-butyl mercaptan.

The inventors have found that thiosulphate salts, when included in low levels in the compositions of the fourth aspect are also surprisingly good intensifiers, producing a marked improvement in corrosion inhibition compared to that achievable with quaternary ammonium compounds of the invention alone. A preferred thiosulphate salt is sodium thiosulphate.

Particularly preferred compositions of this aspect of the invention comprise, in aqueous solution:
20-30 weight % of a quaternary ammonium compound of formula (I), (II) or (III)
2-6 weight % sodium thiosulphate
10-20 weight % butoxyethanol.

In use, the corrosion inhibitor compositions of this aspect of the invention become diluted and are preferably used at a level of between 5 and 2500 ppm/v, i.e., the quaternary ammonium compound itself is preferably used at a level of about 1 to about 500 ppm.

In a fifth aspect, the invention provides a process of protecting a metal surface against corrosion comprising contacting the metal surface with a corrosion inhibitor composition of the fourth aspect. Preferably, the corrosion inhibitor compositions of the present invention reduce corrosion rates to a level of 0.1 mm per year or below as measured by a standard corrosion kettle test.

In a sixth aspect, the invention the use of a corrosion inhibitor of the fourth aspect or a process of the fifth aspect to inhibit corrosion or protect a metal surface in a downhole application, e.g. in a wellbore application, such as an oil drilling application, or subterranean application. In preferred embodiments this process comprises contacting a subterranean zone with a corrosion inhibitor of the fourth aspect or process of the fifth aspect to reduce corrosion rates to a level of 0.1 mm per year or below as measured by a standard corrosion kettle test.

It will be appreciated that the inhibitors of the fourth aspect and processes of the fifth aspect are useful during the course of subterranean operations such as the drilling, cementing, fracturing, maintenance and production, workover, abandonment of a well and other operations associated with subterranean wells.

Embodiments of the invention are described below by way of example only, and with reference to the accompanying figures of which.

EXAMPLES

Raw Materials
Low erucic rapeseed fatty acid, C chain length C16-C20 (predominantly C18 unsaturated).
Triethanolamine
Dimethyl sulphate Synthesis Example 1

470 grams of rapeseed fatty acids were introduced in an inert atmosphere into a stainless steel reactor, and 480 g of PEG 3 triethanolamine (triethanolamine+3EO) were added with stirring (molar ratio of fatty acid/PEG3TEA: 1/1). The mixture was heated for at least 4 hours at 160-180° C. in order to remove the water of the reaction. The progress of the reaction was monitored by an acid/base assay which determines the residual acidity to obtain an esterification of at least 90 to 95% of the fatty acids.

919 g of a brown liquid product, referred to as "esteramine 2" were recovered, consisting essentially of a mixture of unesterified fatty acids and mono-, di- and triesterified amine (small amounts of unreacted triethanolamine ethoxide may also remain).

Quaternization
180 g of dimethyl sulphate were added with stirring at a temperature of 60-90° C. to 800 g of "esteramine 2". After one hour of digestion, the virtually complete absence of residual amine was verified by acid/base assay. 980 g of quaternized esteramine 2 were obtained. The product is then diluted to 90% by adding approximately 110 g of isopropanol. 1090 g of surfactant referred as X3160 were obtained.

The structure of the cationic component of this product approximates to that shown below. However, the product is a mixture of mono-, di- and tri-esters. Furthermore, the ethoxylation at each triethanolamine hydroxyl group varies, so that the final product is a mixture of compounds, in which, on average each hydroxyl group is ethoxylated once.

R1 here corresponds to the hydrocarbyl residue of rapeseed oil fatty acid.

Synthesis Example 2

Fatty Acid Triethanolamine Ester Preparation 493 grams of rapeseed fatty acid was introduced in an inert atmosphere into a stainless steel reactor and 270 g of triethanolamine was added with stirring (molar ratio of fatty acid/TEA:1/1). The mixture was heated for at least 4 hours at 160° C. in order to remove the water of the reaction. The progress of the reaction was monitored, by an acid/base assay which determined the residual acidity, to obtain an esterification of at least 90 to 95% of the fatty acids.

A yellow liquid product, referred to as "enteramine 1" was recovered, consisting essentially of a mixture of unesterified fatty acids and mono-, di- and triesterified amine (small amounts of unreacted triethanolamine may also remain).
Ethoxylation

| Base formula | MW | Moles | Mass |
|---|---|---|---|
| Rapeseed esteramine | 418.4 | 1.0 | 418.4 |
| KOH - 45% in water | 56.1 | 0.017 | 0.981 |
| Ethylene oxide | 44.05 | 4 | 176.2 |

Esteramine and 45% aq KOH were mixed between 25 and 80° C. under nitrogen and stripped of water at 90-100 C and 20-50 mm-Hg pressure with a nitrogen sparge. Nitrogen was used to pressurise the reactor at 5-15 psi. EO was gradually added to the mixture at 155-165° C. and a pressure of about 80 psig. After the EO addition was complete the mixture was allowed to react between 155 and 165° C. for 1 hr or until the reactor pressure indicated a complete reaction. The product was partly neutralized at 50-70° C. with acetic acid to a pH of about 8.
Quaternisation The same method was employed as in Synthesis Example 1.

At the end of the reaction the 10% w/w propan-2-ol was added to improve the handling properties. The surfactant was referred to as X3161.

Synthesis Example 3

This method was the same as above in Synthesis Example 2 but 6 moles of ethylene oxide were added during the ethoxylation stage. At the end of the reaction the 10% w/w propan-2-ol was added to improve the handling properties. The surfactant was referred to as X3162.

The X3161 product is a mixture of mono-, di- and tri-esters, of which one cationic component may have formula (III) as set out above, in which r+q=4 and R1 is the hydrocarbyl residue of rapeseed oil fatty acid. Transesterification during preparation can, however lead to esterification to different extents, and at different positions.

X3162, like X3161, is a mixture of mono-, di- and tri-esters. In this case one cationic component of the mixture may have formula (III) as set out above, with r+q=6 and, again, R1 is the hydrocarbyl residue of rapeseed fatty acid.

Synthesis Example 4

This method was the same as above in Synthesis Example 1 but 373 g rapeseed fatty acids was used as starting material along with 558 g of PEG 6 triethanolamine (triethanolamine+6EO). The molar ratio of fatty acid/PEG6TEA was 1/1.

The mixture was heated in the stainless steel reactor for 10 hours at 180° C.

907 g of brown liquid product, referred to as "esteramine 3", was recovered.

Quaternization was also carried out as in Synthesis Example 1. 149 g dimethyl sulphate was added to 826 g esteramine 3. After two hours of digestion, 975 g of surfactant, referred to as X3226-3 was obtained.

As for X3160 described in Synthesis Example 1', the product is a mixture of mono- di- and tri-esters and the final product is a mixture of compounds but in X3226-3, each hydroxyl group is, on average, ethoxylated twice.

Synthesis Example 5

This method was the same as above in Synthesis Example 1 but 548 g rapeseed fatty acids was used as starting material along with 410 g of PEG 6 triethanolamine (triethanolamine+6EO). The molar ratio of fatty acid/PEG6TEA was 2/1.

The mixture was heated in the stainless steel reactor for 12 hours at 185° C.

935 g of brown liquid product, referred to as "esteramine 4", was recovered.

Quaternization was also carried out as in Synthesis Example 1. 108.2 g dimethyl sulphate was added to 846.6 g esteramine 4. After one hour of digestion, 954.8 g of surfactant, referred to as X3226-M was obtained.

As for X3160 described in Synthesis Example 1, the product is a mixture of mono- di- and tri-esters and the final product is a mixture of compounds but in X3226-M, each hydroxyl group is, on average, ethoxylated twice.
Mono-, Di-, Tri-Ester Components A comparison of the X3226-3 and X3226-M products reveals that the X3226-M surfactant contains a higher proportion of di- and tri-esters relative to mono-esters (i.e. it is enriched in the di- and tri-esters). By comparison the X3226-3 surfactant tends to contain a mono-, di-, tri-ester profile that is more balanced or weighted towards the mono-esters.

This altered ester profile is believed to be due to the 2/1 ratio of fatty acid/PEG6TEA used in the production of X3226-M compared to the 1/1 ratio of fatty acid/PEG6TEA, described in Synthesis Example 4, for the production of X3226-3.

Formulation Examples

Each of the products synthesized above was included in a test formulation having the following composition:

25% of a 90% by weight solution of test compound (i.e. X3161, 3162 or 3160) in isopropanol;
4% sodium thiosulphate;
16% 2-butoxyethanol;
55% water Percentages are by weight of the total composition. The formulations were designated: Formulation A, containing X3160; Formulation B, containing X3161; and Formulation C, containing X3162.

A further set of test formulations was produced corresponding to Formulations A, B and C in which the 4% sodium thiosulphate was omitted.

These formulations were designated: Formulation A—no sodium thisulphate; Formulation B—no sodium thiosulphate; and Formulation C—no sodium thiosulphate.

Corrosion Testing

The corrosion protection afforded by these formulations was evaluated using a corrosion kettle test.

The test was performed using 800 ml of brine (3% NaCl) and 200 ml of odourless kerosene with the temperature set at 70° C. The fluids were sparged with $CO_2$ for 2 hours to remove oxygen from the test fluids prior to starting corrosion rate logging using Linear Polarization Resistance (LPR). Corrosion rates were recorded automatically every 10 minutes. The probes were allowed to corrode for 2 hours before corrosion inhibitor injection (20 ppm/v) to establish a baseline corrosion rate. The test was then left for 16 hours to allow the corrosion rate to equilibrate. Corrosion inhibitor performance was then calculated as percent protection using the baseline and inhibited corrosion rates.

Tests were also performed on X3226-3 and X3226-M surfactants in combination with sodium thiosulphate. In these tests, 20 ppm/v of 25% X3226-3 or X3226-M in water was added at the corrosion inhibitor injection step and 20 ppm/v of 4% sodium thiosulphate solution in water was also added at this stage. Otherwise, the tests were as described above.

Figure 1:
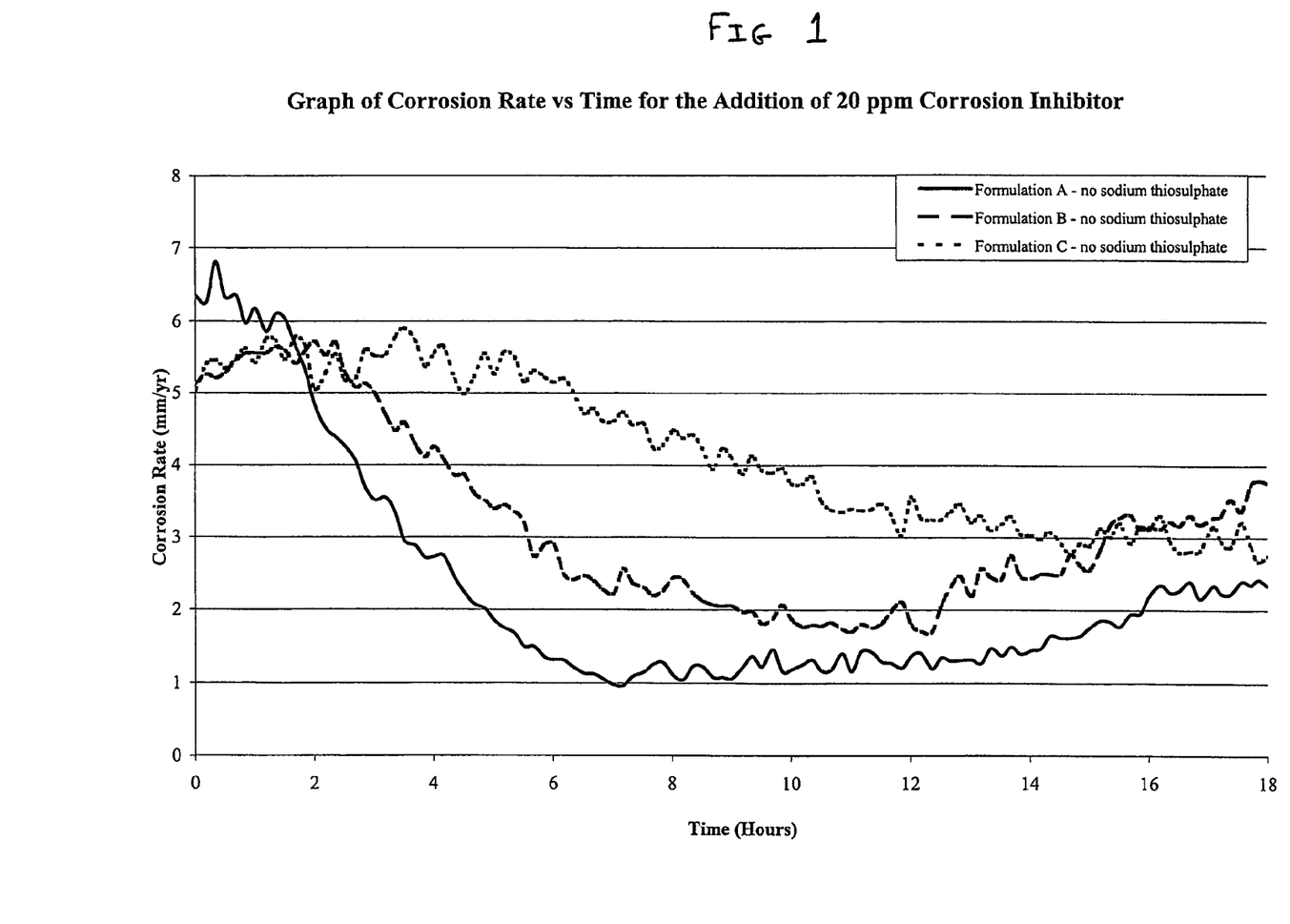
FIG. 1 shows a graph of corrosion rate against time for three different corrosion inhibitor compositions containing quaternary ammonium compounds designated X3160, X3161, or X3162.

A summary of the corrosion test results for the formulations lacking thiosulphate addition is given in Table 1. The results are presented graphically in FIG. 1.

TABLE 1

| Inhibitor | Concentration (ppm/v) | Pre-Corrosion Rate (mm/yr) | Inhibited Corrosion Rate (mm/yr) | % Protection |
|---|---|---|---|---|
| Formulation A - no sodium thiosulphate | 20 | 6.04 | 2.32 | 61.51 |
| Formulation B - no sodium thiosulphate | 20 | 5.59 | 3.54 | 36.74 |
| Formulation C - no sodium thiosulphate | 20 | 5.73 | 2.93 | 48.98 |

Figure 2:
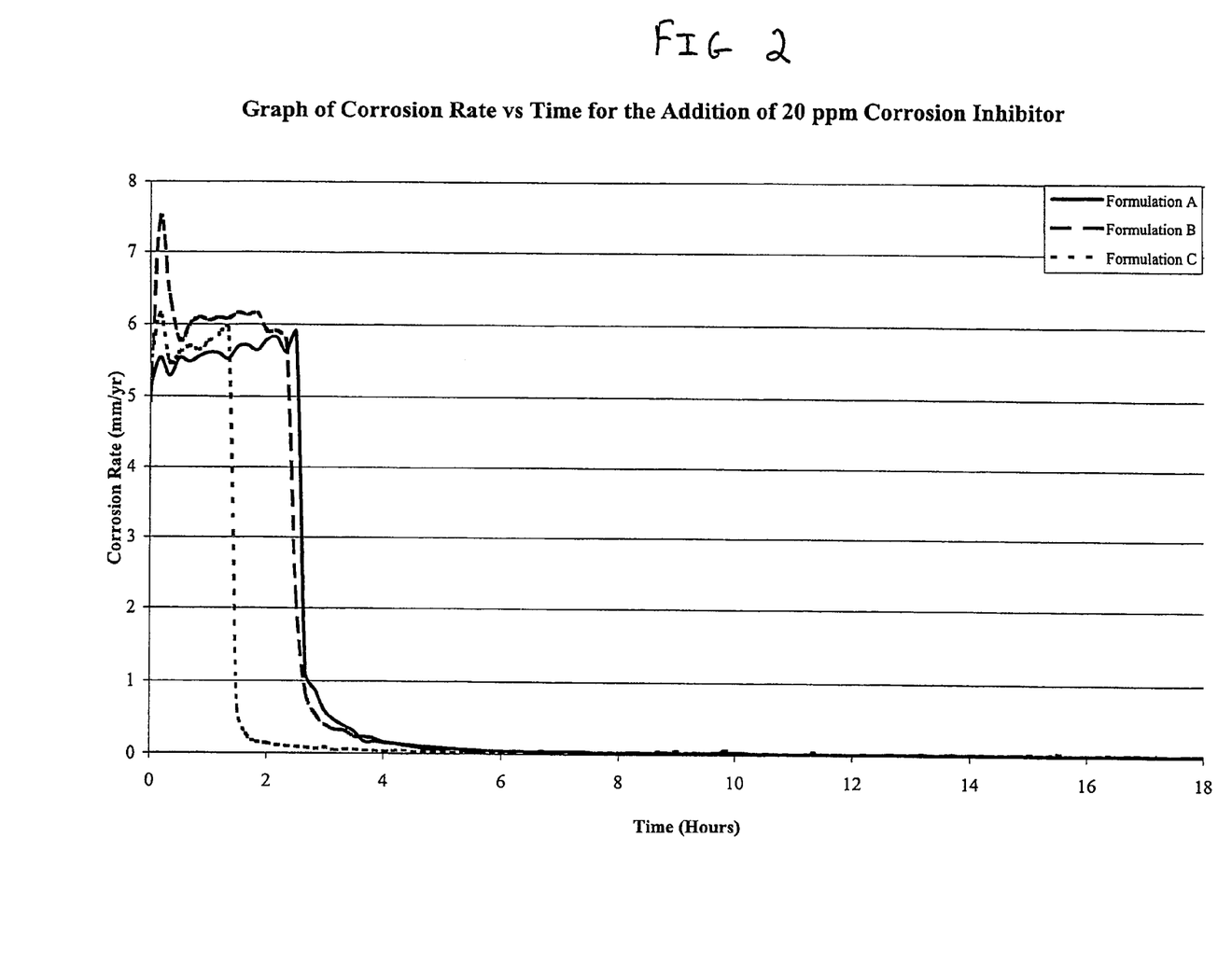
FIG. 2 shows a graph of corrosion rate against time for three corrosion inhibitor compositions containing the same three compounds, and also sodium thiosulphate.

When the formulations including thiosulphate were subjected to the same test, the results were as set out below in Table 2, and results for Formulations A, B and C are represented graphically in FIG. 2.

TABLE 2

| Inhibitor | Concentration (ppm/v) | Pre Corrosion Rate (mm/yr) | Inhibited Corrosion Rate (mm/yr) | % Protection |
|---|---|---|---|---|
| Formulation A | 20 | 5.882 | 0.016 | 99.73 |
| Formulation B | 20 | 5.778 | 0.020 | 99.65 |
| Formulation C | 20 | 5.953 | 0.072 | 98.79 |

TABLE 2-continued

| Inhibitor | Concentration (ppm/v) | Pre Corrosion Rate (mm/yr) | Inhibited Corrosion Rate (mm/yr) | % Protection |
|---|---|---|---|---|
| X3226-3 thiosulphate | 20 | 6.57 | 0.076 | 98.84 |
| X3226-M thiosulphate | 20 | 6.53 | 0.119 | 98.18 |

TABLE

Summary of Kettle Test Results

These results show that the inclusion of a low level of sodium thiosulphate produces a surprising improvement in the corrosion inhibition achievable using the quaternary ammonium compounds of the invention. The formulations including thiosulphate all gave excellent corrosion inhibition. In this test an industry standard corrosion rate is 0.1 mm/yr and all the formulations including thiosulphate reduced corrosion rate to less than 0.1 mm/yr.

The results also surprisingly show that the surfactant containing higher proportions of di- and tri-ester and depleted in mono ester (X3226-M) shows decreased corrosion inhibition performance compared with the surfactant containing more mono-ester component (X3226-3).

Biodegradability Testing

In order to determine the environmental profile of X3160, X3161 and X3162, these compounds were tested for biodegradability using the test procedure set out in detail in OECD Guideline for Testing of Chemicals TG 306 (Biodegradability in Seawater). The results of the tests are set out in Table 3.

TABLE 3

| Product | Biodegradation after 28 days |
|---|---|
| X3160 | 63% |
| X3161 | 60% |
| X3162 | 65% |

It is evident from the results set out above that the compounds tested provide a combination of high levels of protection against corrosion and good biodegradability.

Emulsion Test

The following five products were subjected to an emulsion test:
Formulation A;
Formulation B;
Formulation C;
30% Tall oil fatty acid/diethylene triamine imidazoline acetate salt (CAS number 68153-60-6) (In this formulation there was 22.5% active imidazoline present. This is a standard oilfield imidazoline. The acetate salt of the imidazoline was used as it is water soluble);
22.5% quaternary ammonium compound, benzalkonium chloride (CAS number 68424-85-1).

The activity of the formulations was the same—22.5%.
An emulsion test was then carried out to measure:
Speed of separation of the two phases
Quality of the oil/water interface
Quality of the liquid phases There is no industry standard emulsion test method, but the method below is widely used to screen products and was employed here:

50 mls of brine (3% NaCl) and 50 mls of standard oil (odourless kerosene) were added to an emulsion test tube at room temperature along with 50 ppm/vol of the corrosion inhibitor formulations. The emulsion test tubes were then shaken for 2 minutes to mix the oil and brine phases. After the shake period, the time taken for the two phases to separate was recorded. 5 minutes after the shake period the quality of the interface, oil and water was also recorded.

Similar tests were performed to compare surfactants X3226-3 and X3226-M. These tests used the same brine/kerosene mixture as described above. 20 ppm/vol of the raw surfactant was added to the brine/oil mixture and was shaken 200 times. After shaking, the time taken for the two phases to separate was recorded. 10 minutes after the shake period, the quality of the oil and brine phases was recorded.

Results

The results summarised below demonstrate that Formulations A, B and C have a decreased emulsifying tendency compared to the standard imidazoline and benzalkonium chloride. There was little or no differentiation in the quality of the interface or liquid phases with the exception of the imidazoline aqueous phase which was slightly hazy. However, the speed of separation of formulations A, B and C was significantly quicker compared to the imidazoline and benzalkonium chloride.

The results also show that the surfactant which has a higher proportion of di- and tri-ester (and is depleted in mono-ester), i.e. X3226-M, is less compatible with the oil phase than the X3226-3 surfactant, although the separation times for these two surfactants are comparable.

TABLE 4

| Product | Speed of separation | Interface Quality | Water quality | Oil Quality |
| --- | --- | --- | --- | --- |
| Formulation A | 15 seconds | Sharp/good | Good/Clear | Good/Clear |
| Formulation B | 29 seconds | Sharp/good | Good/Clear | Good/Clear |
| Formulation C | 39 seconds | Sharp/good | Good/Clear | Good/Clear |
| 22.5% Imidazoline | 55 seconds | Sharp/good | Slightly hazy | Good/Clear |
| 22.5% benzalkonium chloride | 201 seconds | Sharp/good | Good/Clear | Good/Clear |
| Surfactant X3226-3 | 190 seconds | Sharp/good | Good/Clear | Slightly Hazy |
| Surfactant X3226-M | 171 seconds | Sharp/good | Good/Clear | Cloudy |

Brine Compatibility Test

Surfactants X3162, X3226-3 and X3226-M were subjected to a standard oilfield brine compatibility test.

Three concentrations of NaCl brine (solution in water) were prepared. The raw surfactant compositions were added in varying amounts to the brine solutions and left to stand for 24 hours at 70° C. A visual assessment of the quality of the solution was then performed. Any precipitate or cloudiness in the solutions is undesirable and is an indicator of incompatibility of the surfactant with the brine. The results are shown in Table 5.

TABLE 5

| Brine | Surfactant | Concentration (ppm) of surfactant | | |
| --- | --- | --- | --- | --- |
| | | 20 | 50 | 100 |
| 3% NaCl | X3162 | Clear | Clear | Clear |
| | X3226-3 | Clear | Clear | Clear |
| | X3226-M | Trace of precipitate | Hazy (some precipitate) | Hazy (some precipitate) |
| 10% NaCl | X3162 | Clear | Clear | Clear |
| | X3226-3 | Clear | Clear | Clear |
| | X3226-M | Slightly Hazy | Hazy | Hazy (some precipitate) |
| 20% NaCl | X3162 | Clear | Clear | Clear |
| | X3226-3 | Clear | Clear | Clear |
| | X3226-M | Clear | Slightly Hazy | Hazy (some precipitate) |

These results indicate that while the X3162 and X3226-3 surfactants are fully compatible with brine solutions at all of the concentrations tested, the X3226-M composition (which is depleted in mono-ester component) is incompatible at most brine concentrations and most levels of surfactant (the only compatibility for this surfactant was seen at 20% brine and 20 ppm X3226-M).

The invention claimed is:

1. A corrosion inhibitor composition comprising a water miscible organic solvent and a quaternary ammonium compound of formula (I):

wherein:
R is an alkyl group containing 1 to 6 carbon atoms, an alkenyl group containing 2 to 6 carbon atoms, an aryl, or aralkyl group;
one of X, Y and Z is a group of formula R1CO and the other two are hydrogen, where R1 is an alkyl or alkenyl group containing 5 to 23 carbon atoms and 0,1,2 or 3 double bonds;
D is a $C_2$ to $C_6$ alkylene group;
E is a $C_2$ to $C_4$ alkylene group;
p, q and r are each, independently, integers from 0 to 20, with the proviso that p+q+r is from 3 to 20; and A− is an anion.

2. A composition according to claim 1, wherein R is a methyl group.

3. A composition according to claim 1 wherein D is a —$CH_2CH_2$— group.

4. A composition according to claim 1 wherein E is a $CH_2CH_2$— group.

5. A composition according to claim 1 wherein p+q+r is from 3 to 10.

6. A composition according to claim 5 wherein p+q+r is from 3 to 6.

7. A composition according to claim 1 wherein the quaternary ammonium cation has formula (II) below:

(II)

wherein each of p, q, r is independently 0, 1, 2 or 3, provided that p+q+r is 3.

8. A composition according to claim 1, wherein the quaternary ammonium cation has formula (III) below:

(III)

wherein q+r lies between 3 and 10.

9. A composition according to claim 8, wherein r+q is 4 or 6.

10. A composition according to claim 1 wherein R1CO is the acyl group of rapeseed oil fatty acid.

11. A composition according to claim 1 wherein the composition comprises a mixture of quaternary ammonium compounds, the mixture containing a higher proportion of mono-ester(s), in which one of the groups X, Y and Z is R1CO and the other groups are hydrogen atoms, than each of di- and tri-ester(s), in which two or three of the groups X, Y and Z are R1CO and the other groups are hydrogen atoms.

12. A composition according to claim 11 wherein the mixture contains at least 40% mono-ester(s).

13. A composition according to claim 1 wherein the composition is an aqueous solution.

14. A composition according to claim 13 which also comprises a corrosion inhibitor intensifier.

15. A composition according to claim 14 comprising about 5 to about 50% by weight of quaternary ammonium compound of formula (I), up to about 10% by weight of intensifier, and up to about 30% by weight of water miscible cosolvent.

16. A composition according to claim 14, wherein the intensifier is a thiosulphate salt.

17. A method of producing a corrosion inhibitor composition comprising a quaternary ammonium compound of formula (I):

(I)

wherein:

R is an alkyl group containing 1 to 6 carbon atoms, an alkenyl group containing 2 to 6 carbon atoms, an aryl, or aralkyl group;

one of X, Y and Z is a group of formula R1CO and the other two are hydrogen, where R1 is an alkyl or alkenyl group containing 5 to 23 carbon atoms and 0, 1, 2 or 3 double bonds;

D is a $C_2$ to $C_6$ alkylene group;

E is a $C_2$ to $C_4$ alkylene group;

p, q and r are each, independently, integers from 0 to 20, with the proviso that p+q+r is from 3 to 20; and A– is an anion, the method comprising alkoxylation of a trialkanolamine followed by esterification of the alkoxylated trialkonolamine with an equimolar amount of R1COOH, quaternisation, and addition of a water miscible organic solvent.

18. A method of producing a corrosion inhibitor composition comprising a quaternary ammonium compound of formula (I):

(I)

wherein:

R is an alkyl group containing 1 to 6 carbon atoms, an alkenyl group containing 2 to 6 carbon atoms, an aryl, or aralkyl group;

one of X, Y and Z is a group of formula R1CO and the other two are hydrogen, where R1 is an alkyl or alkenyl group containing 5 to 23 carbon atoms and 0, 1, 2 or 3 double bonds;

D is a $C_2$ to $C_6$ alkylene group;

E is a $C_2$ to $C_4$ alkylene group;

p, q and r are each, independently, integers from 0 to 20, with the proviso that p+q+r is from 3 to 20; and A– is an anion, the method comprising esterification of a trialkanolamine with an equimolar amount of R1COOH, followed by alkoxylation of the esterified trialkanolamine, quaternisation, and addition of a water miscible organic solvent.

19. A process of protecting a metal surface against corrosion comprising contacting the metal surface with a corrosion inhibitor composition of claim 1.

20. A process of protecting a metal surface against corrosion in a downhole application comprising:

contacting a downhole metal surface with a corrosion inhibitor composition of claim 1.

* * * * *